(12) United States Patent
Burt

(10) Patent No.: US 7,468,056 B2
(45) Date of Patent: Dec. 23, 2008

(54) COLOSTOMY BAG AND METHOD OF USE

(76) Inventor: Margaret Burt, 129 Intervale Rd., Canterbury, NH (US) 03224

( * ) Notice: Subject to any disclaimer, the term of this patent is extended or adjusted under 35 U.S.C. 154(b) by 0 days.

(21) Appl. No.: 11/799,143

(22) Filed: May 1, 2007

(65) Prior Publication Data
US 2008/0275410 A1  Nov. 6, 2008

(51) Int. Cl.
A61F 5/44 (2006.01)

(52) U.S. Cl. .............. 604/330; 604/317; 604/323; 604/324; 604/326; 604/327

(58) Field of Classification Search ............ 604/317, 604/323, 324, 326, 327, 331–333, 337–339, 604/341, 350, 355
See application file for complete search history.

(56) References Cited

U.S. PATENT DOCUMENTS

| | | | | |
|---|---|---|---|---|
| 4,121,589 A | * | 10/1978 | McDonnell | 604/328 |
| 4,300,560 A | * | 11/1981 | Steer et al. | 604/335 |
| 4,319,571 A | * | 3/1982 | Winchell | 604/342 |
| 4,490,145 A | * | 12/1984 | Campbell | 604/333 |
| 4,516,974 A | | 5/1985 | Davis | |
| D295,220 S | | 4/1988 | Kay | |
| 5,330,454 A | * | 7/1994 | Klingler et al. | 604/338 |
| 5,372,594 A | | 12/1994 | Colacello et al. | |
| 5,470,325 A | * | 11/1995 | Fundock | 604/332 |
| 5,690,622 A | * | 11/1997 | Smith et al. | 604/333 |
| 5,938,647 A | * | 8/1999 | Smith | 604/332 |
| 6,007,525 A | * | 12/1999 | Martell | 604/333 |
| 6,231,553 B1 | | 5/2001 | Hulett | |
| 2003/0236509 A1 | | 12/2003 | Silvestrini | |
| 2005/0131360 A1 | | 6/2005 | Villefrance et al. | |

* cited by examiner

Primary Examiner—Tatyana Zalukaeva
Assistant Examiner—Ilya Y Treyger
(74) Attorney, Agent, or Firm—T.L. Garrett, PLC; Tanya L. Garrett

(57) ABSTRACT

A colostomy bag with a vent and a method for venting gas collected in the colostomy bag. A dual vent and cap assembly attached to a colostomy bag vents gas trapped in the bag either continuously or as periodically desired by a user. A method for venting gas collected in the colostomy bag provides that replacement and/or cleaning of the colostomy bag is reduced. Also, a method of using a disposable sleeve in combination with a clip may be used to hygienically clean the colostomy bag.

15 Claims, 8 Drawing Sheets

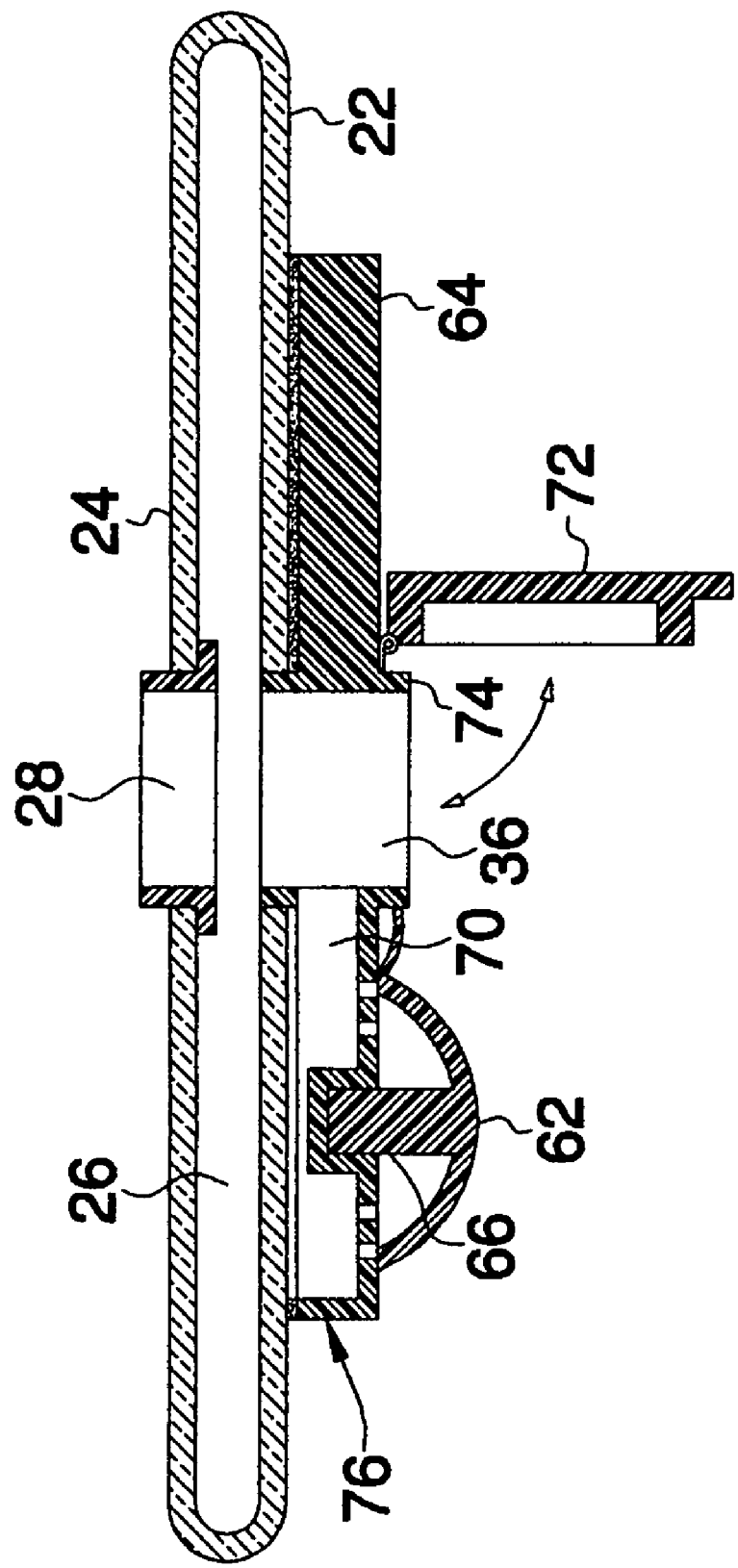

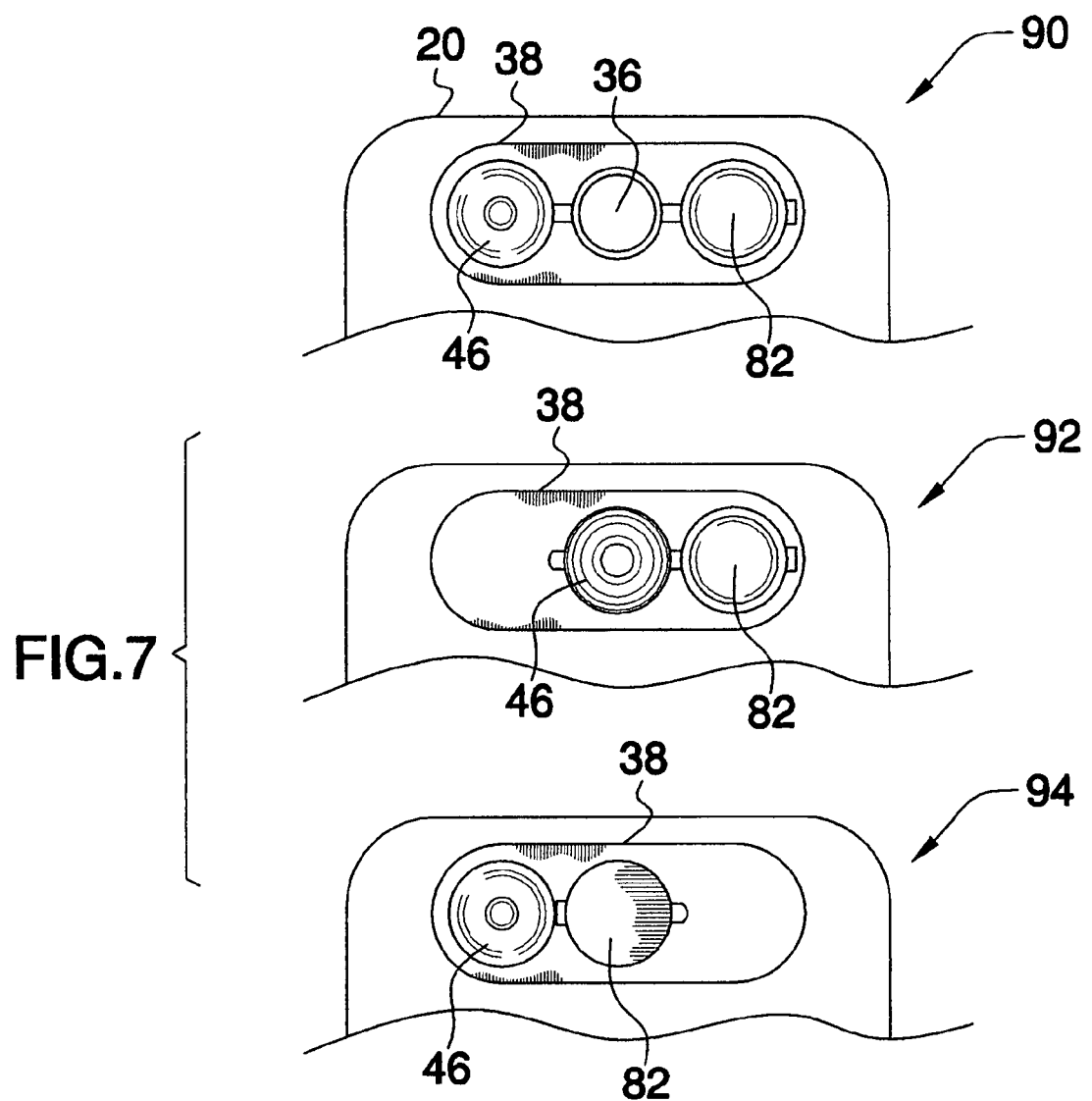

COLOSTOMY BAG AND METHOD OF USE

FIELD OF THE INVENTION

The present invention generally relates to human waste removal for use in the field of colostomy bags.

BACKGROUND

After the surgical removal of the large intestine of a patient due to, for example, colon cancer, severe acute obstruction, trauma, gunshot wounds, and/or the like, a patient may require a means for removing bodily waste. A colostomy bag is generally used by a patient after the surgical removal of the large intestine performed during a colostomy. A colostomy is a surgical procedure in which an artificial permanent opening, referred to as a stoma, is provided and through which the colon may be artificially evacuated. Bodily waste exits the body by passing through the stoma into a colostomy bag. After the bag is full, the bag is usually detached from the stoma, discarded, and replaced. The frequent removal and replacement is burdensome, inconvenient, and often irritating to the patient.

Further, the colostomy bag is generally fitted with a clamp such that the waste may be removed while the bag is still attached to the body of the user. During use, gases and other waste from the body fill the bag and may be released through removal of the clamp. The gas causes the bag to blow up and becomes uncomfortable and very bulky when worn by the user. The gas can be so great as to pull the bag away from the body. This causes discomfort to the user and/or exposes the user to infection.

The discomfort caused by known colostomy bags limits the mobility of the user. The user may often become fearful of moving about because of a perceived embarrassment and discomfort should the bag be dislodged. Further, the known colostomy bags do not enable easy and/or convenient discharge of waste. For example, a person who is outdoors, or otherwise does not have access to a restroom or private area, may be inhibited from removing waste and/or cleaning the known colostomy bag. Because of the perceived embarrassment, discomfort, and other inconveniences of the known colostomy bags, the mobility of the user may become limited.

Further, a colostomy bag generally requires at least two hands for handling during cleaning and/or removal and changing of the bag. Accordingly, many patients that use the known colostomy bag require assistance. For example, persons that are bedridden, paralyzed due to, for example, a stroke or spinal cord injuries, have limited use of their upper extremities, are missing an arm, or the like need assistance handling the known colostomy bag.

The use of devices and methods relating to colostomy bags are disclosed in U.S. Pat. No. 2003/0236509 A1 issued in the name of Silvestrini entitled "Colostomy Bag with Gas Release Valve and Method for releasing Gas Collected in the Colostomy Bag" which is herein incorporated by reference in its entirety; U.S. Pat. No. 6,231,553 B1 issued in the name of Hulett entitled "Colostomy Bag"; U.S. Pat. No. 5,372,594 issued in the name of Colacello et al. entitled "Colostomy Pouche with Vent Valve"; U.S. Pat. No. 4,516,974 issued in the name of Davis entitled "Universal Vent Device and Method for Ostomy Appliances"; U.S. Pat. No. Des. 295,220 issued in the name of Kay entitled "Drain Valve for Ostomy Receptacles"; and U.S. Pat. No. 2005/0131360 A1 issued in the name of Villefrance et al. entitled "Drainable Ostomy Pouch with Integrated Closure".

A need, therefore, exists for a colostomy bag with a vent for release of gas and a method for venting gas such that the colostomy bag may not need to be cleaned and/or frequently changed. Further, a need exists for a colostomy bag and method for venting gas from the colostomy bag wherein the colostomy bag is easier to handle than conventional bags. Additionally needed is a bag that is easily cleaned by use of a single hand of a user.

SUMMARY OF INVENTION

The present invention generally relates to a colostomy bag with a vent and a method for venting gas collected in the colostomy bag. More specifically, the present invention relates to a dual vent and cap assembly attached to a colostomy bag for venting gas trapped in the bag either continuously or as desired by a user. In addition, the present invention relates to a method for venting gas collected in a colostomy bag such that replacement and/or cleaning of the colostomy bag is reduced. Also, a method of using a disposable sleeve in combination with a clip may be used to hygienically clean the colostomy bag.

BRIEF DESCRIPTION OF THE DRAWINGS

These and other objects, features and advantages of the present invention will become apparent from the following detailed description and the appended drawings in which:

FIG. 3a illustrates a copy FIG. 3 taken across section line 3-3 in accordance with one embodiment of the invention.

FIG. 7 illustrates an enlarged view of a vent piece, a port hole, and a cap in an open, vented and closed position respectively in accordance with an embodiment of the invention.

DETAILED DESCRIPTION OF THE INVENTION

The present invention generally relates to a colostomy bag with a dual vent and cap assembly and a method for releasing gas collected in the colostomy bag. More specifically, the present invention relates to a vent piece attached to a colostomy bag for release of gas in the bag. Venting of the bag allows for releasing gas collected in a colostomy bag such that replacement and/or cleaning of the colostomy bag is reduced.

The invention provides a colostomy bag that allows the bag to be emptied with one hand. The colostomy bag provides an efficient system for emptying and rinsing a colostomy bag.

In one embodiment of the invention, the bag measures 0.5 inch in height, 2.5 inches in length, and 1.75 inches in width.

Figure 1:
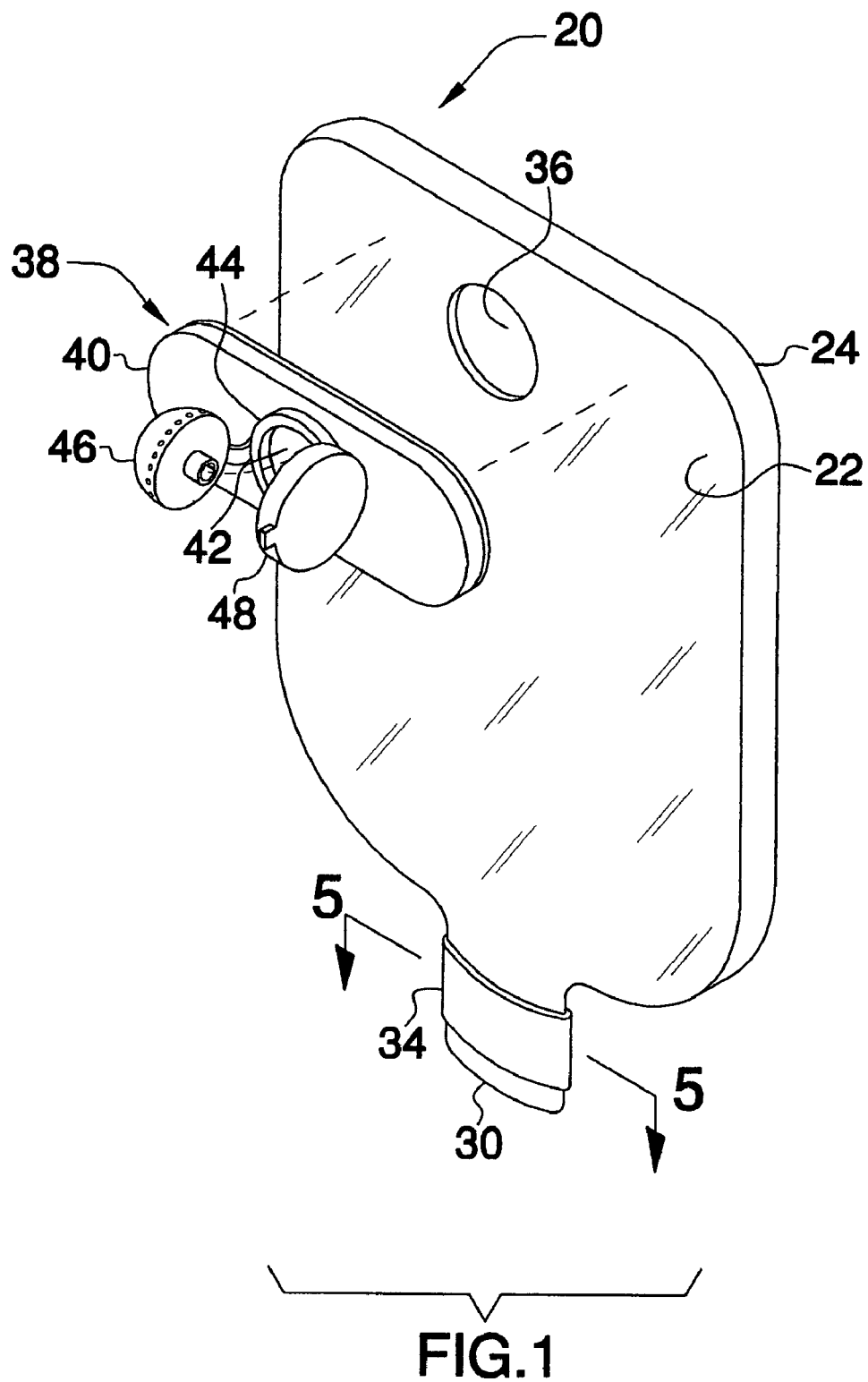
FIG. 1 illustrates a perspective of a colostomy bag in accordance with one embodiment of the invention.
Figure 2:
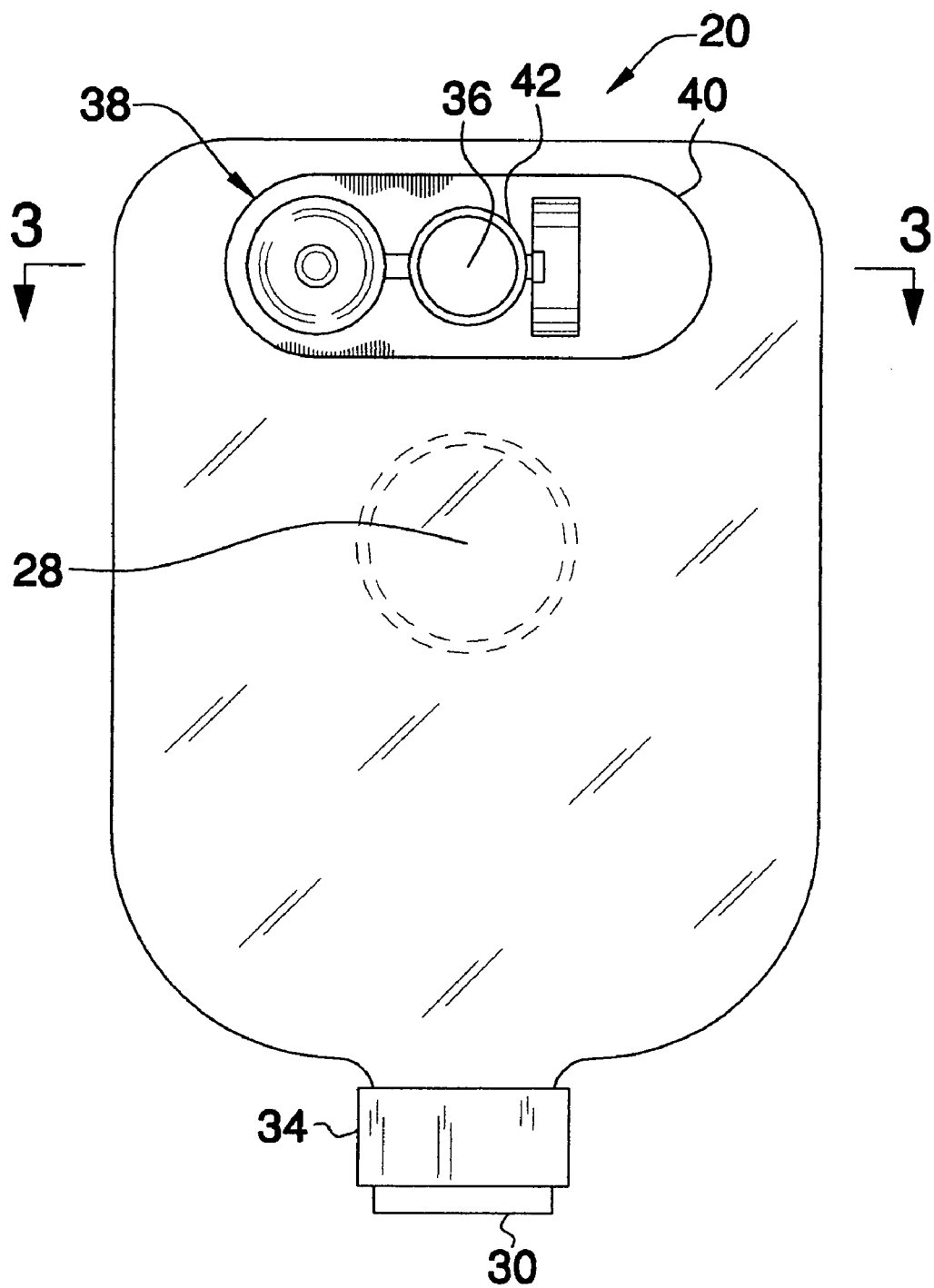
FIG. 2 illustrates a front elevational view of the colostomy bag of FIG. 1.
Figure 4:
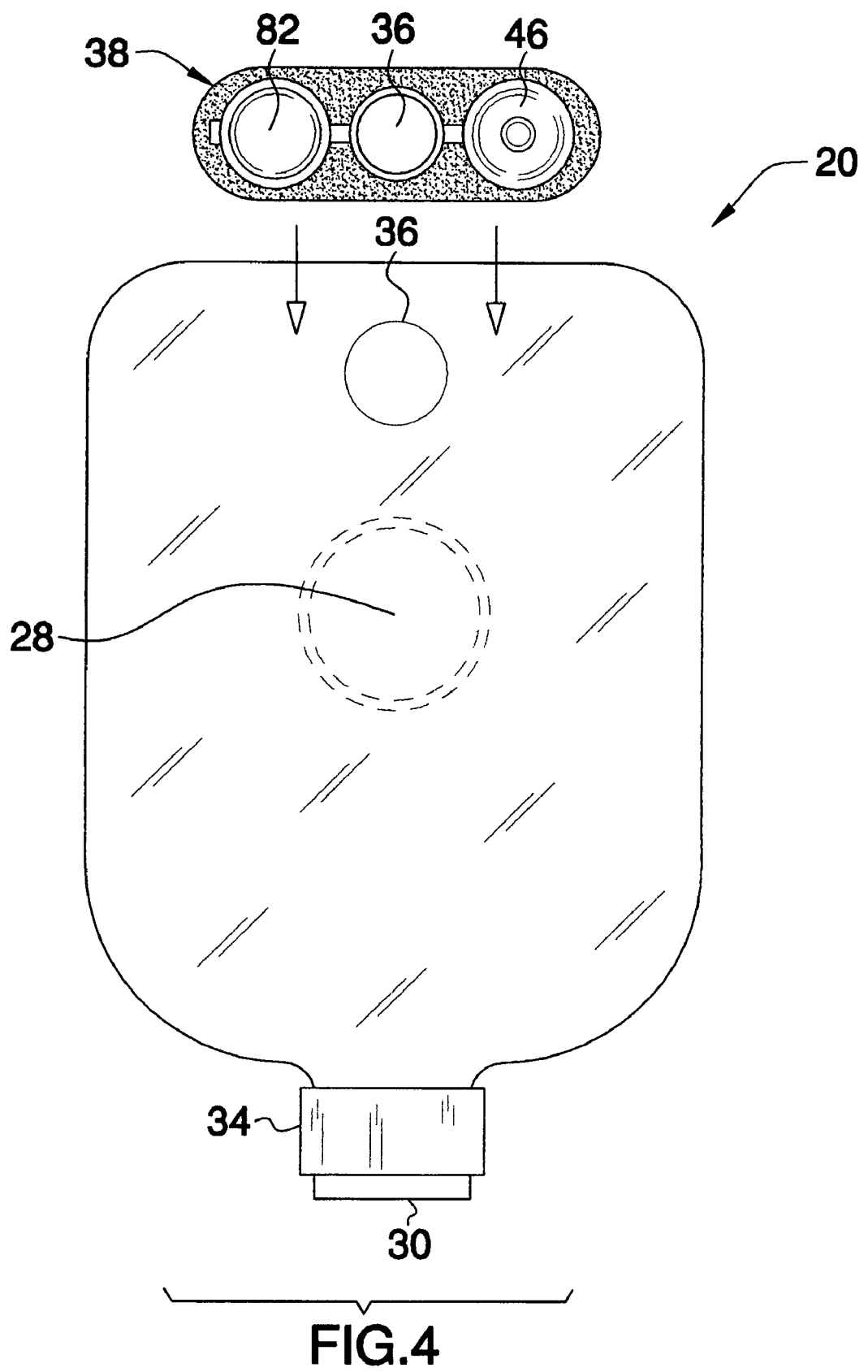
FIG. 4 illustrates a front elevational view of a colostomy bag in accordance with one embodiment of the invention.
Figure 6:
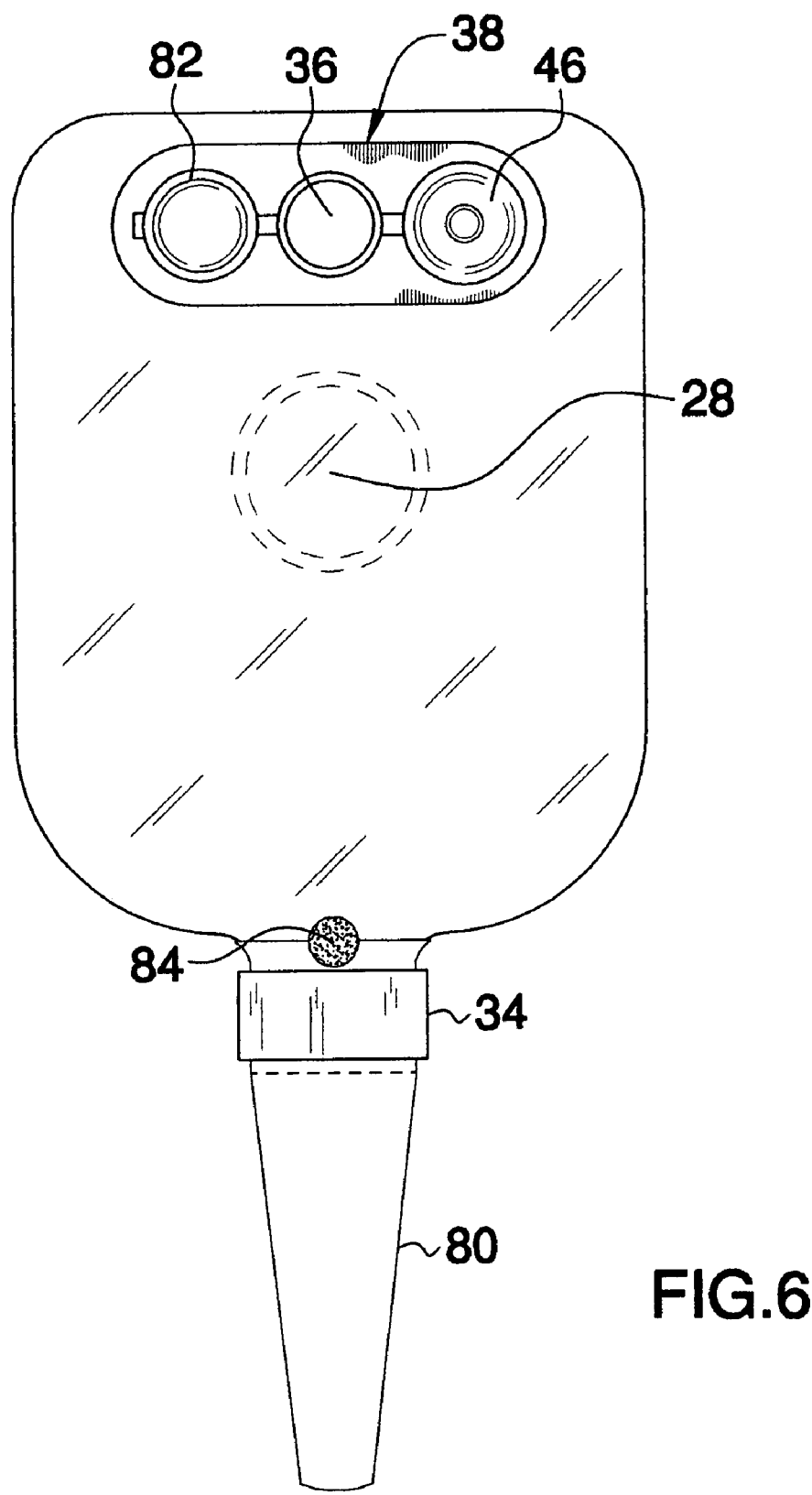
FIG. 6 illustrates a front elevational view of a colostomy bag including a sleeve adapted to aid in the disposal of waste inside the colostomy bag in accordance with one embodiment of the invention.

Referring now to the drawings wherein like numerals refer to like parts, FIG. 1 generally illustrates a perspective view of a colostomy bag 20. FIGS. 2, 4, and 6 illustrates a front perspective view of the colostomy bag 20. The colostomy bag 20 may have an exterior surface including a front and a rear side, 22, 24, respectively and an interior 26. The colostomy bag 20 may preferably be constructed with a reuseable, liquid impermeable material, such as, for example, plastic or the like. The colostomy bag 20 is generally illustrated in FIG. 1 having an oblong shape. However, the colostomy bag 20, may be constructed in the shape of a sphere, square, or the like. Further, the colostomy bag may be constructed from any one or more of various materials apparent to those skilled in the art without departing from the spirit of the present invention.

As shown in FIGS. 2, 3, 3a, 4, and 6, the colostomy bag 20 may have a first opening 28 on the rear side of the exterior surface that sealingly engages the bag to a stoma. The first opening 28 may be configured for receiving human waste via a stoma. A stoma is an artificial permanent opening in the abdominal wall created, for example, during a surgical procedure. The first opening 28 may be increased in diameter to adjust the opening for the stoma of a particular patient. The first opening may be increased in diameter by simply cutting along the edge of the opening with scissors, a knife, or the like (not shown). For example, the opening may be increased in size to an extent indicated by a diameter illustrated in FIG. 1.

The colostomy bag 20 may receive human waste from, for example, a large intestine of the patient. The human waste may be evacuated from the patient, through the stoma and through the first opening 28 to the interior 26 of the colostomy bag 20. The waste may continue to be collected in the colostomy bag 20 until the colostomy bag 20 is full. After the colostomy bag 20 is full, the colostomy bag 20 may be removed and/or replaced. Of course, the colostomy bag 20 may be removed and/or replaced prior to the colostomy bag 20 being filled.

The colostomy bag 20 may further have a bottom end 30 located a distance from the first opening 28. The bottom end 30 of the colostomy bag 20 may have a second opening 32 through which contents received in the interior 26 of the colostomy bag 20 may be emptied. For example, after the colostomy bag 20 is full, the colostomy bag 20 may be removed and the contents therein may be emptied through the second opening 32 of the bottom end of the colostomy bag. The second opening 32 may be releasably closed with a clip 34.

Figure 5:
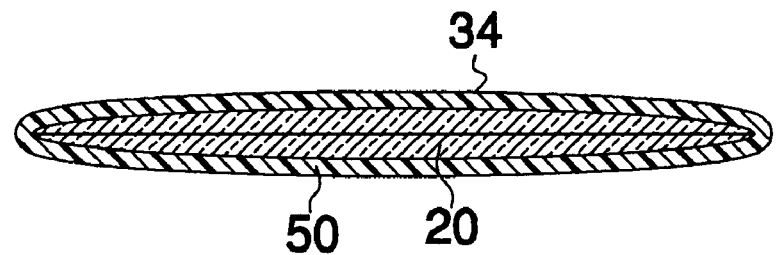
FIG. 5 illustrates a cross-sectional view of a band closure clip and adhesive adapted to form a seal retaining contents of the colostomy bag when the bag is in a closed position.
Figure 5A:
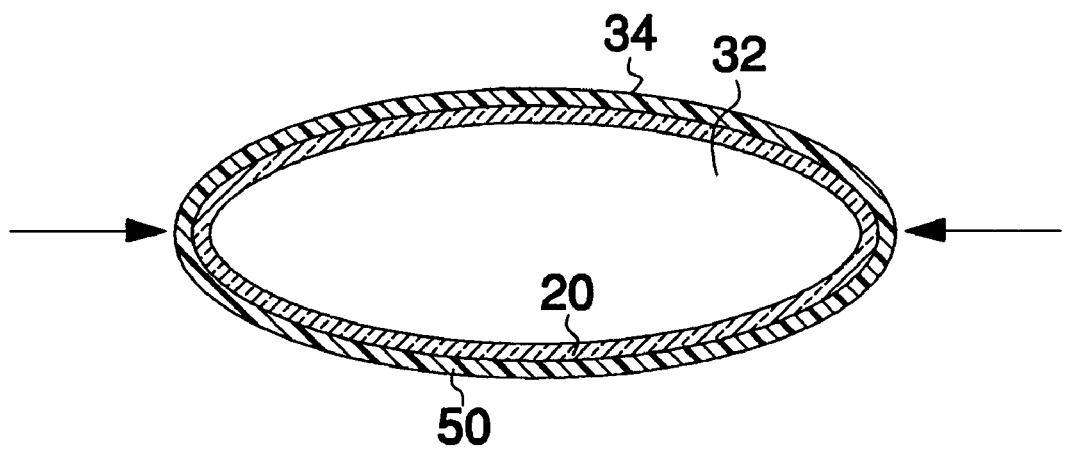
FIG. 5a illustrates a cross-sectional view of a band closure clip and adhesive adapted to form a seal retaining contents of the colostomy bag when the bag is in a closed position.

The band closure clip 34 facilitates opening and closing the bottom end 30 of the bag 30 as shown in more detail in FIGS. 5 and 5a.

Alternatively, the second opening 32 may be permanently sealed. Further, the colostomy bag 20 may be constructed with only one opening, such as, for example, the opening, i.e. without the second opening 32. Of course, if the second opening is permanently sealed, or if the colostomy bag is constructed with only two openings, the contents received in the interior 32 of the colostomy bag 20 may not be emptied. The colostomy bag 20 having only two openings may not be emptied and reused but simply discarded and replaced.

Additionally, the colostomy bag 20 may have a third opening defining a port hole 36 in the front side 22 of the colostomy bag 20.

The bag 20 includes a dual vent cap assembly 38 for venting or sealing the bag 20 in communication with the port hole 36 allowing access to an interior region of the bag as shown in FIGS. 1-3, 4, 6, and 7. The dual vent cap assembly 38 fits onto the port hole 36 and sealingly engages the port hole 36 for connection to the bag 20.

The dual vent and cap assembly 38 includes a support base 40 having an opening 42 found therethrough encircled by a uniform raised rim 44 protruding outwardly therefrom. As shown in FIGS. 1-4, and 6-7, the support base opening 42 is circular.

A hemi-spherical shaped vent piece 46 and a cap 48 are attached to a respective portion of the raised rim 44 and are each adapted to sealingly cover the centrally disposed opening 42 by forming a seal with the raised rim 44. The support base 40 is affixed to a top portion of the front side 22 of the colostomy bag 20 via an adhesive backing 50 (shown in more detail in FIGS. 3-3a).

Figure 3:
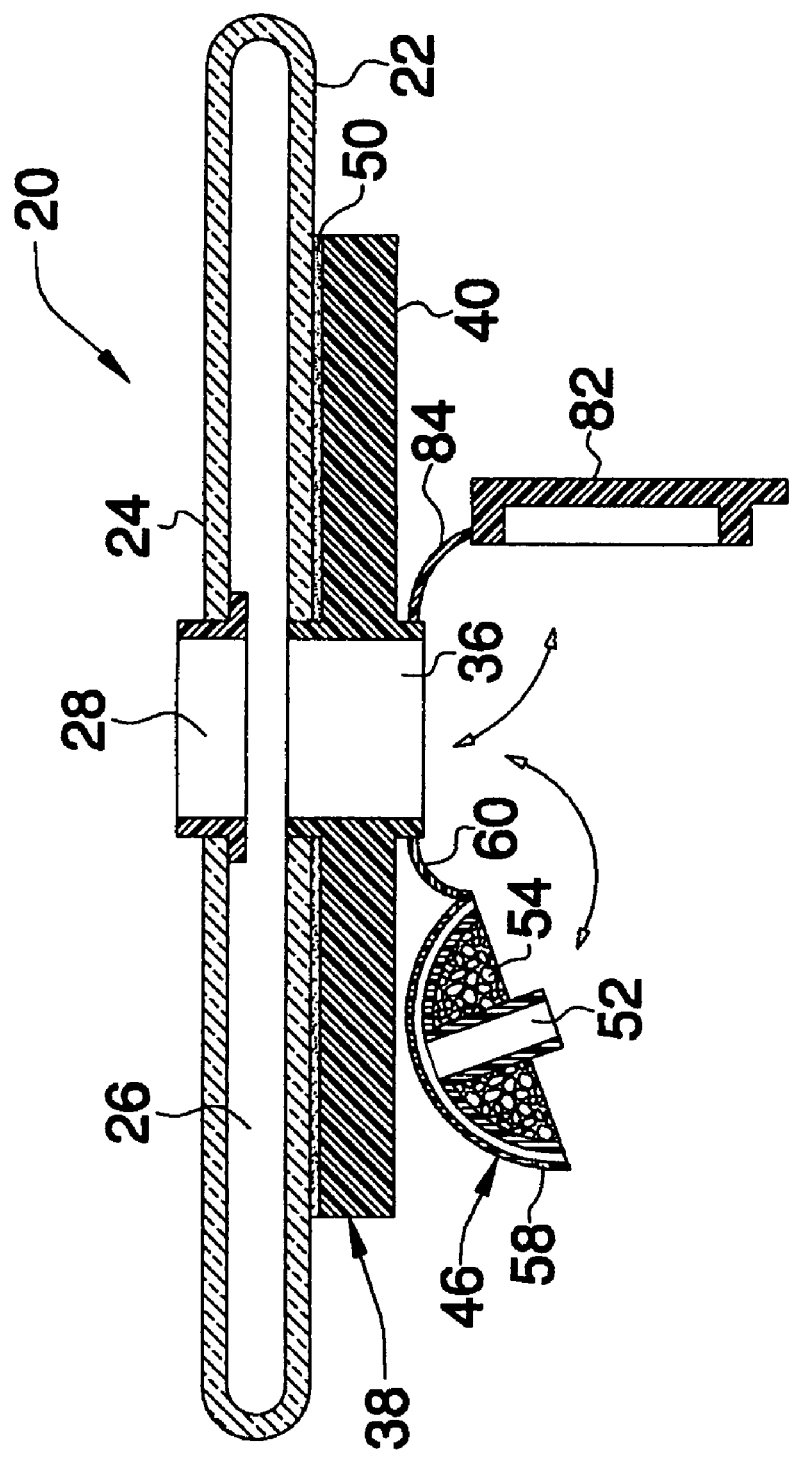
FIG. 3 illustrates a cross-sectional view of the colostomy bag of FIG. 2 taken across section line 3-3 in accordance with one embodiment of the invention.

In an embodiment of the invention shown in FIGS. 1 and 3, the vent piece 46 includes a central tube 52 extending axially through the hemi-spherical vent piece 46 and further includes a gas absorbent material 54 such as charcoal for absorbing colostomy gases therein. Additionally, a plurality of vent openings 56 in open communication with the tube 52 are disposed through a peripheral wall 58 defining the hemi-spherical profile of the vent piece 46. The vent piece 46 may attach to the rim 44 by use of a first resilient flexible retention member 60, wherein the vent piece 46 remains loosely connected to the vent piece 46 until the vent piece 46 is used to cover the port hole 36.

The vent piece 46 is a hemi-spherical member, preferably made of hard plastic with the tube 52 embedded axially therethrough. The tube 52 is in open communication with the port hole 36 when the vent piece 46 sealingly engages through a friction fit to the rim 44.

The dual vent and cap assembly 38 includes a cap 82 loosely attached to the rim 44 via a second resilient flexible retention member 84. The cap 82 may be removed to expose the port hole 36 to the interior of the bag wherein gas may be released to the atmosphere. Further, one of any number of different caps apparent to those skilled in the art may be incorporated with the colostomy bag without departing from the spirit of the present invention.

An alternative embodiment of the dual vent cap assembly shown in FIG. 3a, a vent piece 62 is oriented in a continuous venting configuration and may be retained in a fixed position relative to a support base 64 within a complementary formed recess 66 within the support base 64. The vent piece 62 has a plurality of vent openings 68 in open communication with a side port 70 associated with the port hole 36 to allow continuous venting of the colostomy bag gases. A cap 72 is hingeably attached to a rim 74 of a dual vent cap assembly 76.

The vent piece 62 allows continuous be release of gas from the interior 26 of the colostomy bag 20. Venting of the bag 20 prevents colostomy bag accidents, such as leakage or bursting.

The dual vent and cap assemblies 38, 76 generally illustrated in FIGS. 1-4, and 6 is in an open position.

Clip 34 is attached to the bottom opening 32 on the colostomy bag 20. The clip 34 opens when inward pressure is applied at edges of the clip 34 and retracts to a shut position when pressure is released and is affixed to the bag 20 with the adhesive backing 50 for secure attachment.

A user may apply pressure to the edges of the clip 34 to compress the clip 34. By compressing the clip 34, a gap defined by second opening 32 may be created as shown in more detail in FIG. 5a. The gap 32 may allow the gas (not shown) and by contents to escape the interior 28 of the colostomy bag 20.

Referring to FIG. 5, the clip 34 is generally illustrated in a closed position. After the user releases the clip 34 the clip may close the gap 78, thereby sealing the interior 28 of the colostomy bag 20 as shown in FIG. 5.

In one embodiment of the invention shown in FIG. 6, a disposable colostomy draining sleeve 80 is provided to remove contents of the bag 20 in a hygienic manner thereby preventing spillage while emptying the bag. Thus, the bag 20 may prevent soiling of outer-wear garments and decrease the occurrence of unpleasant odors and bacteria.

Draining sleeve 80 is a long, plastic tube that connects to the bag via one or more adhesive patches 84 above or over the clip 34. The draining sleeve 80 makes emptying of the bag 20 into a toilet bowl easier without spilling.

To empty the bag 20, the user attaches the draining sleeve 80 to the bottom of the bag 20 and employs one hand to open the clip 34, allowing the contents to drain.

After use, the draining sleeve 80 is discarded. The sleeve 80 may be made of a biodegradable material that may be easily flushed down a toilet.

After the colostomy bag 20 is full, the human waste received in the colostomy bag 20 may be emptied by releasing the sealed second opening 32. The colostomy bag may be cleaned as shown and the second opening 32 may be closed again. To rinse the bag 20, the user removes the cap 72, 82 from the port hole 36, squeezes in water and opens the clip 34 to drain the contents of the bag 20. An open configuration 90 exposing port hole 36 is shown in FIG. 7. To vent the bag 20 as shown in FIG. 7, the user connects the vent piece to the port hole 36, which allows pent-up gases to be released from the bag as shown in vented configuration 92 of FIG. 7. A closed configuration 94 is shown in FIG. 7 wherein the cap 82 covers port hole 36. To close the port hole 36, the cap 82 is sealed.

In use, the patient or caregiver squeezes the clip 34 at the bottom of the bag to create an opening. As used herein, a user is defined as a patient or a caregiver. The user then closes the clip 34 and opens the port hole 36 at the top of the bag. Water would be squeezed in to rinse the unit. The emptying process is then repeated. The patient would be able to secure the vent in position to release any built up gasses. The user may use the bag in either a closed or a vented configuration.

Use of the colostomy bag allows for top to bottom emptying of the bag and facilitates cleaning.

Alternatively, after the colostomy bag is full, the colostomy bag may be removed, discarded, and/or replaced.

The appealing features of the bag 20 include ease of use, efficacy, practicality, and convenience. The bag 20 provides a more user-friendly way to care for disposing of colostomy bag contents. It can be operated with one hand and can thereby provide peace of mind for the user. In addition, the bag is more hygienic than conventional bags. The bag thus provides a patient using a colostomy bag with more independence in the patient's care by enabling a patient to empty the colostomy bag with one hand without assistance.

Accidents, such as bursting or leaking, will be averted with the use of the bag. The bag will therefore make the daily care of elimination equipment a less cumbersome and more simple procedure.

While several aspects have been presented in the foregoing detailed description, it should be understood that a vast number of variations exist and these aspects are merely an example, and it is not intended to limit the scope, applicability or configuration of the invention in any way. Rather, the foregoing detailed description provides those of ordinary skill in the art with a convenient guide for implementing a desired aspect of the invention and various changes can be made in the function and arrangements of the aspects of the technology without departing from the spirit and scope of the appended claims.

What is claimed is:

1. A colostomy bag comprising:
an exterior surface including
a rear side having a first opening that operates to sealingly engage the colostomy bag to a stoma,
a front side has a second opening defining a port hole adapted to mate with a dual vent end cap assembly;
an interior adapted to collect human waste;
a dual vent and cap assembly adapted to allow venting of gasses from the interior of the colostomy bag including
a support base located on the outer surface of the colostomy bag,
an opening disposed through the support base encircled by a uniform raised rim protruding outwardly therefrom,
a hemi-spherical vent piece that operates to vent colostomy gasses from the interior of the colostomy bag, and
a cap attached to a respective portion of the uniform raised rim, wherein the hemi-spherical shaped vent piece and the cap are each adapted to sealingly cover the centrally disposed opening by forming a seal with the raised rim; and
a bottom end having a second opening disposed at the bottom end of the colostomy bag through which contents received in the interior of the colostomy bag are emptied.

2. The colostomy bag of claim 1, further comprises:
a band closure clip that facilitates opening and closing the bottom end of the bag, wherein the clip operates tog expose the second opening when pressure is applied thereto and to sealingly engage the bottom end of the colostomy bag thereby closing the second opening when pressure is not applied thereto.

3. The colostomy bag of claim 1, further comprising:
an adhesive backing adhered to support a rear portion of the support base that operates to affix the support base to a top portion of the front side of the colostomy bag.

4. The colostomy bag of claim 1, wherein the vent piece comprises:
a central tube extending axially through the hemi-spherical vent piece, wherein the central tube is in open communication with the port hole when the vent piece covers the port hole; and
a plurality of vent openings in open communication with the tube, wherein the plurality of openings are disposed through a peripheral wall defining a hemi-spherical profile of the vent piece.

5. The colostomy bag of claim 4, wherein the vent piece attaches to the uniformed raised rim by use of a first resilient flexible retention member.

6. The colostomy bag of claim 1, wherein the vent piece further comprises:
a gas absorbent material for absorbing colostomy gasses therein.

7. The colostomy bag of claim 6, wherein the gas absorbent material comprises:
charcoal.

8. The colostomy bag of claim 1, wherein the dual vent cap assembly comprises:
a vent piece oriented in a continuous venting configuration and having a portion retained in a fixed position relative to the support base within a complimentary formed recess within the support base; and
a plurality of vent openings in open communication with a side port associated with the port hole to allow continuous venting of the colostomy bag gasses.

9. The colostomy bag of claim 1, wherein the cap is hingeably attached to the uniform raised rim of the dual vent cap assembly.

10. The colostomy bag of claim 1, further comprising;
    a draining sleeve adapted to remove contents of the colostomy bag in a hygienic manner thereby preventing spillage while emptying the bag.

11. The colostomy bag of claim 10, wherein the draining sleeve comprises:
    a plastic tube that connects to the bottom end of the bag through use of at least one adhesive patch fixedly attached to the exterior of the colostomy bag.

12. The colostomy bag of claim 10, wherein the draining sleeve comprises:
    a biodegradable material.

13. A method of using a colostomy bag of claim 1 including:
    providing a colostomy bag including an exterior surface including a rear side having a first opening that operates to sealingly engage the colostomy bag to a stoma, a front side has a second opening defining a port hole adapted to mate with a dual vent end cap assembly, an interior adapted to collect human waste, a dual vent and cap assembly adapted to allow venting of gasses from the interior of the colostomy bag including a support base located on the outer surface of the colostomy bag, and a bottom end having a second opening disposed at the bottom end of the colostomy bag through which contents received in the interior of the colostomy bag are emptied, and a draining sleeve adapted to remove contents of the bag in a hygienic manner thereby preventing spillage while emptying the bag;
    opening the closure band clip thereby draining the contents of the bad into the draining sleeve;
    closing the closure band clip; and
    discarding the draining sleeve.

14. The method of claim 13, further comprising:
    rinsing the bag with water.

15. The method of claim 14, wherein the method of rinsing the bag comprises:
    exposing the port hole;
    squeezing water through the port hole; and
    opening the clip to drain the contents of the bag.

* * * * *